US011407701B2

United States Patent
Ochoa Gómez et al.

(10) Patent No.: US 11,407,701 B2
(45) Date of Patent: Aug. 9, 2022

(54) METHOD FOR CONTINUOUS PRODUCTION OF 2,3-BUTANEDIOL

(71) Applicant: FUNDACION TECNALIA RESEARCH & INNOVATION, San Sebastián (ES)

(72) Inventors: José Ramón Ochoa Gómez, Miñano (ES); Susana Pérez Gil, Miñano (ES); María Del Mar Díaz De Guereñu Zabarte, Miñano (ES); Inés Rincón Arroyo, Miñano (ES)

(73) Assignee: FUNDACION TECNALIA RESEARCH & INNOVATION, Donostia—San Sebastián (ES)

( * ) Notice: Subject to any disclaimer, the term of this patent is extended or adjusted under 35 U.S.C. 154(b) by 217 days.

(21) Appl. No.: 16/762,469

(22) PCT Filed: Nov. 8, 2018

(86) PCT No.: PCT/EP2018/080627
§ 371 (c)(1),
(2) Date: May 7, 2020

(87) PCT Pub. No.: WO2019/092112
PCT Pub. Date: May 16, 2019

(65) Prior Publication Data
US 2021/0188746 A1    Jun. 24, 2021

(30) Foreign Application Priority Data
Nov. 9, 2017   (EP) .................................... 17382756

(51) Int. Cl.
*C07C 29/145*   (2006.01)
*C07C 31/20*    (2006.01)
(Continued)

(52) U.S. Cl.
CPC ............. *C07C 29/145* (2013.01); *B01J 8/06* (2013.01); *B01J 19/1825* (2013.01);
(Continued)

(58) Field of Classification Search
None
See application file for complete search history.

(56) References Cited

U.S. PATENT DOCUMENTS

| | | | |
|---|---|---|---|
| 6,262,317 B1 * | 7/2001 | Becker ................... | B01J 8/0278 568/861 |
| 8,921,616 B2 * | 12/2014 | Kizaki .................. | C07C 29/143 568/861 |
| 9,975,827 B2 * | 5/2018 | Ochoa Gomez ...... | C07C 29/145 |

FOREIGN PATENT DOCUMENTS

| | | | |
|---|---|---|---|
| JP | 2015227298 A | 12/2015 | |
| WO | WO 2003/042142 A1 | 5/2003 | |

(Continued)

OTHER PUBLICATIONS

International Seach Report and Written Opinion dated Jan. 15, 2019 for PCT International Application No. PCT/EP2018/080627, 12 pages.
(Continued)

*Primary Examiner* — Jennifer A Leung
(74) *Attorney, Agent, or Firm* — Squire Patton Boggs (US) LLP

(57) ABSTRACT

The present invention relates to a method for continuous production of 2,3-butanediol by hydrogenation of 3-hydroxybutanone with hydrogen in the presence of a heterogeneous hydrogenation catalyst filled in one or more fixed-bed flow tubular reactor systems comprising one or more tubes with an inner diameter from 1 mm to 6 mm.

15 Claims, 1 Drawing Sheet

(51) Int. Cl.
*B01J 8/06* (2006.01)
*B01J 19/18* (2006.01)
*B01J 23/46* (2006.01)

(52) U.S. Cl.
CPC .... *B01J 23/462* (2013.01); *B01J 2219/00038* (2013.01); *B01J 2219/00051* (2013.01); *C07C 31/207* (2013.01)

(56) References Cited

FOREIGN PATENT DOCUMENTS

WO    WO 2016/012634 A1    1/2016
WO    WO 2016/097122 A1    6/2016

OTHER PUBLICATIONS

Duan, et al: "Vapor-phase hydrogenation of acetoin and diacetyl into 2,3-butanediol over supported metal catalysts", Catalysis Communications, May 22, 2017; vol. 99, pp. 53-56.
Henkel, et al: "Reactor types and their industrial applications", Encyclopedia of Industrial Chemistry, Ullmann's Principles of Chemical Reaction Engineering and Plant Design Jan. 1, 1992; pp. 87-120, XP002072387.

\* cited by examiner

METHOD FOR CONTINUOUS PRODUCTION OF 2,3-BUTANEDIOL

This application is a national-phase entry under 35 U.S.C. § 371 of International Patent Application No. PCT/EP2018/080627 (filed Nov. 8, 2018), which claims the benefit of European Patent Application No. EP 17382756.9 (filed Nov. 9, 2017).

TECHNICAL FIELD

The present invention is related to a method for continuous production of 2,3-butanediol by hydrogenation of 3-hydroxybutanone with hydrogen in the presence of a heterogeneous hydrogenation catalyst, using fixed-bed flow multi (tubular) reactor systems with an inner diameter between 1 and 6 mm.

BACKGROUND OF THE INVENTION 2,3-butanediol (from now on named 2,3-BDO) is a chemical which has important present and potential industrial applications, e.g. as antifreeze, as raw material for methyl ethyl ketone and 1,3-butadiene manufacturing by dehydration, and even as liquid fuel due to its heating value of 27198 kJ·kg$^{-1}$ which is comparable to those of methanol (22081 kJ·kg$^{-1}$) and ethanol (29055 kJ·kg$^{-1}$). Other potential applications include the manufacture of printing inks, perfumes, fumigants, moistening and softening agents, explosives and plasticizers, and as a carrier for pharmaceuticals. Also, it could be used as chain extender in the manufacturing of polymers such as polyurethanes, polyesters and polycarbonates.

Almost the totality of the 2,3-BDO manufacturing processes described are based on fermentation of carbohydrates using many bacterial species. However, all these methods have in common as main drawbacks a very low 2,3-BDO productivity, usually ranging from 1 to 3 g/L/h, and a low 2,3-BDO titer in the final culture broth, usually below 120 g/L, and much more usually below 100 g/L. The latter fact, together with the highly complex chemical composition of the culture broth, lead to cumbersome methods for isolation and purification of 2,3-BDO with the corresponding economic penalties.

There are also some chemical routes for obtaining 2,3-BDO. Recently, three production methods of 2,3-BDO from acetoin (also named 3-hydroxybutanone) have been described.

Thus, the PCT patent application WO2016097122 discloses the manufacturing of 2,3-BDO by electroreduction of acetoin in aqueous media using porous cathodes coated with metal hydrogenation catalysts in the presence of an inorganic salt (which provides the suitable electrical conductivity for electrochemical reduction). The process works at room temperature in both divided and undivided cells. However, incomplete acetoin conversions of 72% are needed for obtaining acetoin selectivities higher than 95% (cf. example 6 of WO2016097122) Therefore, the incomplete acetoin conversion in combination with the use of the inorganic salt lead to a cumbersome recovery and purification procedure.

Besides, the PCT patent application WO2016012634 discloses a method for obtaining 2,3-BDO by hydrogenation of 3-hydroxybutanone (i.e. acetoin) in an aqueous medium using heterogeneous catalysts based on nickel and noble metals. This process allows obtaining 2,3-BDO in yields and selectivities as high as 98% at hydrogen pressures higher than 2 MPa and temperatures higher than 75° C. However, reaction times higher than 2 h are needed for full conversions which results in low 2,3-BDO productivities.

Lastly, Duan et al. discloses a process to produce 2,3-butanediol by vapor-phase catalytic hydrogenation of acetoin and diacetyl over supported metal catalysts such as Ni, Co, Cu, and Ag in a fixed-bed flow tubular reactor. The authors are silent about the reactor dimensions. This process allows obtaining 90.2% conversion of acetoin and 90.1% yield of 2,3-butanediol using Ni/SiO$_2$ as a catalyst in an H$_2$ flow at 150° C. and at 0.1 MPa. However, these results are obtained at a high H$_2$/acetoin molar ratio of 16.4 (16.4-fold the stoichiometric one) and with contact times between 0.5 h and 1.67 h. Consequently, 2,3-BDO productivities are low and additionally a purification procedure is needed to separate acetoin from 2,3-BDO. (H. Duan, et al. "Vapor-phase hydrogenation of acetoin and diacetyl into 2,3-butanediol over supported metal catalysts". *Catalysis Communications*, 2017. Vol. 99, pp. 53-56).

Therefore, from what is known in the art it is derived that there is still the need of providing a highly productive process for obtaining 2,3-BDO from acetoin in higher yield and selectivity.

SUMMARY OF INVENTION

Inventors have provided a highly productive method for the continuously production of 2,3-butanediol by hydrogenation of 3-hydroxybutanone. In particular, the present inventors have surprisingly found that by using one or more fixed-bed flow (multi)tubular reactor systems with an inner diameter from 1 mm to 6 mm, 2,3-BDO is continuously produced in high conversions and high yields by liquid- or vapor-phase hydrogenation of acetoin with hydrogen in the presence of a heterogeneous hydrogenation catalyst and contact times and hydrogen/acetoin molar ratios as low as 6 s and 2.3, respectively, leading to very high productivities.

In the process of the present invention the general operation mode comprises feeding continuously through the top of one or more fixed-bed flow (multi)tubular reactor(s) filled with a hydrogenation catalyst pure molten acetoin or a solution of acetoin in a solvent together with a hydrogen flow. The reactor is heated at a suitable temperature to speed up the hydrogenation. The stream leaving the reactor is cooled at room temperature and the liquid fraction is analyzed for the contents in acetoin and 2,3-BDO by HPLC.

As shown in the examples provided below, by means of the process of the present invention is possible to achieve both an acetoin conversion higher than 95% and a 100% 2,3-BDO selectivity with contact times below 10 s leading to productivities of at least 70 times greater than those of the processes of the current state of the art. In particular, the process of the present invention allows achieving 100% of acetoin conversion and 100% 2,3-BDO selectivity when a fixed-bed flow tubular reactor having an inner diameter of 1.75 mm is used and the process is performed at a 250° C. and at a pressure of hydrogen of 5 MPa.

While not wishing to be bound by any particular theory, it is believed that these surprising very good results are due to the small diameter of the tubular reactor favoring a close contact between the reactants and the catalytic sites, thereby preventing reaction limitation by poor mass transference as well as the existence of preferential flow channels leading to poor reactant-catalyst contact.

Thus, a first aspect of the invention relates to a method for continuous production of 2,3-butanediol, by hydrogenation of 3-hydroxybutanone with hydrogen in the presence of a heterogeneous hydrogenation catalyst filled in one or more fixed-bed flow tubular reactor systems, with each reactor system comprising one or more tubes, wherein the inner diameter of each tube is from 1 mm to 6 mm; wherein the method comprising feeding continuously 3-hydroxybutanone and hydrogen into the fixed-bed flow tubular reactor system.

BRIEF DESCRIPTION OF THE FIGURES

FIG. 1 shows a fixed-bed flow multitubular reactor system comprising 16 tubes, each one 10 cm in length with an inner diameter of 1.75 mm.

DETAILED DESCRIPTION OF THE INVENTION

All terms as used herein in this application, unless otherwise stated, shall be understood in their ordinary meaning as known in the state of the art. Other more specific definitions for certain terms as used in the present application are as set forth below and are intended to apply uniformly throughout the specification and claims unless an otherwise expressly set out definition provides a broader definition.

For purposes of the present invention, any ranges given include both the lower and the upper end-points of the range. Ranges given, such as temperatures, pressure, times, and the like, should be considered approximate, unless specifically stated.

As it is mentioned above, the present invention relates to more productive method to produce continuously 2,3-butanediol by hydrogenation of 3-hydroxybutanone using one or more fixed-bed tubular reactor systems.

The terms "2,3-BDO" or "2,3-butanediol" have the same meaning, and are used interchangeably.

The terms "acetoin" or "3-hydroxybutanone" have the same meaning, and are used interchangeably.

The terms "molecular hydrogen", "hydrogen" or "$H_2$" have the same meaning, and are used interchangeably.

The term "acetoin conversion" refers to the amount of acetoin transformed into another chemical compound relative to the initial amount of acetoin. In the specific case of a continuous process, it refers to the amount of acetoin transformed into another chemical compound relative to the initial amount of acetoin after one pass into the reactor. In the context of the invention, the conversion is expressed as a percentage and it can be calculated by means of equation (1):

$$C(\%) = (N_f - N_{out}) * 100 / N_f \quad (1)$$

where C is the acetoin conversion, $N_f$ are the moles of acetoin/h in the feed into the reactor system and $N_{out}$ are the moles of acetoin/h at the outlet of the reactor system.

The term "selectivity to 2,3-BDO formation" refers to the number of moles of 2,3-BDO obtained relative to the moles of acetoin converted. In the context of the invention, the selectivity is expressed as a percentage and it can be calculated by means of equation (2):

$$S(\%) = N_{BDO} * 100 / (N_f - N_{out}) \quad (2)$$

where S is the 2,3-BDO selectivity, $N_{BDO}$ are the moles of 2,3-BDO/h at the outlet of the reactor system and $N_f$ and $N_{out}$ are as previously defined.

The number of tubes in a reactor system will depend on the desired productivity of the process. In an embodiment, the method is carried out in one or more fixed-bed flow tubular reactor systems comprising from 1 to 25,000 tubes. In an embodiment, the method is carried out in one or more fixed-bed flow tubular reactor systems which comprises two or more parallel tubes having the same lengths and internal diameters, through which the feed rate is evenly distributed. In an embodiment, the inner diameter of each tube is from 1.5 mm to 4 mm. In an embodiment, the length of each tube is from 5 cm and 5 m; preferably from 8 cm and 1 m. In an embodiment, the method is carried out in more than one reactor system and the systems are arranged both in parallel or in series. In an embodiment, the method is carried out in more than one reactor system connected in series and the reaction conditions of pressure, temperature and contact time in each reactor are the same. In another embodiment, the method is carried out in more than one reactor system connected in series and the reaction conditions of pressure, temperature and contact time in each reactor are different. In a particular example, a tubular reactor system comprising 16 tubes, each one 10 cm in length with an inner diameter of 1.75 mm is depicted in FIG. 1. Using the experimental conditions of the example 2 of the present invention, this small reactor system of lab size that fits inside a hand is able to produce 0.942 kg/day of 2,3-BDO. An arrangement in parallel of 100 reactor systems of this type affording for 1600 tubes will produce 94.2 kg/day, i.e. 31.4 tons/y operating during 8000 h/y. The 100 reactor systems can be contained in a small room of 3.5 m×0.15 m×0.05 cm, 0.02625 m³. The total effective volume of the 1600 tubes is $3.85 \cdot 10^{-4}$ m³, resulting in a productivity of 10.20 ton/h/m³.

The process of the present invention can yield an acetoin conversion equal to or higher than the following percentages: 90%, 91%, 92%, 93%, 94%, 95%, 96%, 97%, 98%, 99%, 99.5%, 99.9%, and 100%. In addition, the process of the present invention can yield a selectivity to 2,3-BDO formation equal to or higher than the following percentages: 95%, 96%, 97%, 98%, 99% and 100%.

In an embodiment, the method comprises feeding pure molten 3-hydroxybutanone into the reactor system. In an embodiment, the method comprises feeding 3-hydroxybutanone into the reactor system as a solution in a solvent selected from the group consisting of water, ($C_1$-$C_4$)-alkyl alcohol, and mixtures thereof. In an embodiment, the method comprises feeding 3-hydroxybutanone into the reactor system as a solution in water. In an embodiment, the method comprises feeding 3-hydroxybutanone into the reactor system as a solution in an ($C_1$-$C_4$)-alkyl alcohol selected from the group consisting of methanol, ethanol, propanol, 2-propanol, 1-butanol, 2-butanol, sec-butanol and tert-butanol.

In an embodiment, the method is carried out at a reaction temperature from 75° C. to 275° C., preferably from 100° C. to 250° C.

In an embodiment, the method is carried out at a reaction pressure from 0.1 MPa to 5 MPa of hydrogen preferably from 0.1 MPa to 2.5 MPa of hydrogen.

In an embodiment, the method is carried out at a contact time between the reactants and catalyst from 0.5 s to 10 s, preferably from 1 s to 8 s.

In an embodiment, the method is carried out at a $H_2$/acetoin molar ratio from 1 to 5, preferably from 1.5 to 3.

The catalyst can be any one of the hydrogenation catalysts typically used to reduce ketones to alcohols. Non limitative examples of hydrogenation catalysts are Raney Ni, and metal supported catalysts wherein the metal is selected from the group consisting of Ru, Pt, Pd, and Rh, and the support is selected from the group consisting of carbon, graphite, graphene, graphene oxide, alumina and silica. In an embodiment, the catalyst is a metal supported catalyst wherein the metal is Ru and the support is carbon, silica or alumina.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

Examples 1-5

Following the general operation mode above described, a 50 wt % aqueous solution of acetoin (purity 98%) solution in water was fed into a fixed-bed flow (multi)tubular reactor system consisting of a tube 10 cm in length fully filled with a commercial catalyst of carbon-supported Ru with a Ru load of 5 wt % (Ru(5%)/C) under the experimental conditions given in Table 1. The catalyst bulk density was 0.50 g·mL$^{-1}$. Tube inner diameters and results are also given in Table 1. Conversions and selectivities were calculated according equations (1) and (2), in which $N_{BDO}$ and $N_{out}$ were calculated from the concentrations of acetoin and 2,3-BDO on the condensed fraction liquid at the outlet of the reactor system as determined by HPLC.

As it can be seen in Table 1, 100% selectivities are achieved in all cases with conversions ranging between 90% and 99% for contact times 5.2 s.

Outstanding 2,3-BDO productivities are obtained. For instance, a 2,3-BDO productivity of 2.89 ton/h/m$^3$ is achieved under experimental conditions of example 4. Using the process according to WO2016012634 A1 (example 37) a 74.5-fold lower 2,3-BDO productivity of 0.04 ton/h/m$^3$ is obtained at 125° C. but with the penalty of a higher hydrogen pressure of 5 MPa, 10-fold higher. No data about the dimensions of the tubular reactor used in the process described by Duan et al. are given. However, taking the lower contact time of 0.5 h used and the best value of 2,3-BDO yield (90.1%) reported at 150° C. by these researchers, a 2,3-BDO productivity 562.5-fold lower than that obtained in example 3 of the present invention can be estimated. The process of the present invention has a productivity surprisingly huge in comparison with those of the current state of the art.

TABLE 1

| | Reaction conditions | | | | | Con- tact time (s) | Results | |
|---|---|---|---|---|---|---|---|---|
| Ex. | Di$^a$ (mm) | T (° C.) | P$_{H2}$ (MPa) | Q$_f$ (ton/ h/m$^2$)$^b$ | MR$^c$ | | C$^d$ (%) | S$^e$ (%) | P$^f$ (ton/ h/m$^3$) |
| 1 | 4 | 250 | 5 | 2.006 | 2.3 | 2.1 | 90 | 100 | 8.23 |
| 2 | 1.75 | 250 | 5 | 1.995 | 2.3 | 2.1 | 100 | 100 | 10.20 |
| 3 | 4 | 150 | 0.5 | 0.400 | 2.3 | 3.2 | 90 | 100 | 1.85 |
| 4 | 4 | 150 | 0.5 | 0.600 | 2.3 | 2.1 | 97 | 100 | 2.98 |
| 5 | 4 | 125 | 1.5 | 0.600 | 2.3 | 5.2 | 96 | 100 | 2.95 |

$^a$Inner diameter of the tubular reactor
$^b$Specific feed rate of a 50 wt % aqueous solution of acetoin, relative to the cross-sectional area of the tube TABLE 1-continued

| | Reaction conditions | | | | | Con- tact time (s) | Results | |
|---|---|---|---|---|---|---|---|---|
| Ex. | Di$^a$ (mm) | T (° C.) | P$_{H2}$ (MPa) | Q$_f$ (ton/ h/m$^2$)$^b$ | MR$^c$ | | C$^d$ (%) | S$^e$ (%) | P$^f$ (ton/ h/m$^3$) |

$^c$H$_2$/acetoin molar ratio
$^d$Acetoin conversion
$^e$2,3-Butanediol selectivity
$^f$2,3-BDO productivity Example 6

This example shows that the process of the present invention can be effectively carried out at a hydrogen pressure as low as 0.1 MPa. Following the general operation mode above described, a 50 wt % acetoin solution in water was fed into a reactor system consisting of 6 tubes 10 cm in length arranged in series. The inner diameter of each tube was 1.75 mm. All tubes were operated at 150° C. and were fully filled with the same catalyst than in the previous examples. The feed flow rate was 1.047 ton/h/m$^2$ relative to the cross-sectional surface of a tube. The H$_2$/acetoin molar ratio was 2.3 with a hydrogen pressure of 0.1 MPa. Results are given in Table 2. Conversions and selectivities were determined by HPLC as described in examples 1-5. As it can be seen, a 96.6% conversion and a 100% selectivity are achieved with a total contact time of 9 s.

It is apparent for a skilled in the art that a 100% conversion could be achieved by increasing the number of tubes, by increasing the contact time sequentially from the first to the last tube, or by increasing in the same way the temperature in each tube, or by a combination of both. It is also apparent for a skilled in the art that a 100% conversion could be achieved with a number of tubes lower than those used in these examples by increasing sequentially from the first to the last tube the contact time and/or the temperature in each tube.

TABLE 2

| Tube | Contact time$^a$ (s) | C$^b$ (%) | S$^c$ (%) |
|---|---|---|---|
| 1 | 1.5 | 40.0 | 100 |
| 2 | 3.0 | 74.8 | 100 |
| 3 | 4.5 | 84.4 | 100 |
| 4 | 6.0 | 90.6 | 100 |
| 5 | 7.5 | 94.4 | 100 |
| 6 | 9.0 | 96.6 | 100 |

$^a$Accumulated contact time
$^b$Accumulated acetoin conversion
$^c$Accumulated 2,3-BDO selectivity

REFERENCES CITED IN THE APPLICATION

1. The PCT patent application WO2016097122
2. The PCT patent application WO2016012634
3. H. Duan, et al. "Vapor-phase hydrogenation of acetoin and diacetyl into 2,3-butanediol over supported metal catalysts". *Catalysis Communications*, 2017. Vol. 99, pp. 53-56).

The invention claimed is:
1. A method for continuous production of 2,3-butanediol, by hydrogenation of 3-hydroxybutanone with hydrogen in the presence of a heterogeneous hydrogenation catalyst filled in one or more fixed-bed flow tubular reactor systems comprising one or more tubes, wherein the inner diameter of each tube is from 1 mm to 6 mm; wherein the method comprising feeding 3-hydroxybutanone and hydrogen into the one or more fixed-bed flow tubular reactor systems.

2. The method according to claim 1, wherein the number of tubes in each reactor system is from 1 to 25,000.

3. The method according to claim 1, wherein the one or more fixed-bed flow tubular reactor systems comprise two or more parallel tubes having the same lengths and internal diameters.

4. The method according to claim 1, wherein the inner diameter of each tube is from 1.5 mm to 4 mm.

5. The method according to claim 1, wherein the length of each tube is from 5 cm to 5 m.

6. The method according to claim 1, wherein the method comprises feeding 3-hydroxybutanone into the one or more fixed-bed flow tubular reactor systems as a liquid.

7. The method according to claim 1, wherein the method comprises feeding 3-hydroxybutanone into the one or more fixed-bed flow tubular reactor systems as a solution in a solvent selected from the group consisting of water, ($C_1$-$C_4$)-alkyl alcohol, and mixtures thereof.

8. The method according to claim 7, wherein the ($C_1$-$C_4$)-alkyl alcohol is selected from the group consisting of methanol, ethanol, propanol, 2-propanol, 1-butanol, 2-butanol, sec-butanol and tert-butanol.

9. The method according to claim 1, wherein the reaction temperature is from 75° C. to 275° C.

10. The method according to claim 1, wherein the reaction pressure is from 0.1 MPa to 5 MPa of hydrogen.

11. The method according to claim 1, wherein the contact time between reactants and the catalyst is from 0.5 s to 10 s.

12. The method according to claim 1, wherein the molar ratio $H_2$/3-hydroxybutanone is from 1 to 5.

13. The method according to claim 1, wherein the catalyst is selected from group consisting of Raney Ni and a metal supported catalyst, wherein the metal is selected from the group consisting of Ru, Pt, Pd, and Rh, and the support is selected from the group consisting of carbon, graphite, graphene, graphene oxide, alumina and silica.

14. The method according to claim 1, wherein the method is carried out in more than one of the one or more fixed-bed flow tubular reactor systems and the one or more fixed-bed flow tubular systems are arranged in parallel or in series.

15. The method according to claim 14, wherein the method is carried out in more than one of the fixed-bed flow tubular reactor systems connected in series and the reaction conditions of pressure, temperature and contact time in each of the one or more fixed-bed flow tubular reactor systems are the same or different.

* * * * *